(12) United States Patent
Oeelund et al.

(10) Patent No.: US 9,913,759 B2
(45) Date of Patent: Mar. 13, 2018

(54) WOUND DRESSING

(71) Applicant: Coloplast A/S, Humlebaek (DK)

(72) Inventors: Jakob Oeelund, Alleroed (DK); Bjarke Stroem-Hansen, Ballerup (DK); Carsten Sletten, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 64 days.

(21) Appl. No.: 14/442,401

(22) PCT Filed: Nov. 8, 2013

(86) PCT No.: PCT/DK2013/050369
§ 371 (c)(1),
(2) Date: May 13, 2015

(87) PCT Pub. No.: WO2014/075684
PCT Pub. Date: May 22, 2014

(65) Prior Publication Data
US 2016/0270965 A1    Sep. 22, 2016

(30) Foreign Application Priority Data

Nov. 15, 2012 (DK) .................................. 2012 70704
Mar. 21, 2013 (DK) .................................. 2013 70166

(51) Int. Cl.
*A61F 13/02* (2006.01)
*A61F 13/00* (2006.01)

(52) U.S. Cl.
CPC .......... *A61F 13/022* (2013.01); *A61F 13/025* (2013.01); *A61F 13/0209* (2013.01);
(Continued)

(58) Field of Classification Search
CPC .................. A61F 13/02; A61F 13/025; A61F 2013/00089; A61F 2013/00285
(Continued)

(56) References Cited

U.S. PATENT DOCUMENTS

| 5,244,457 | A | * | 9/1993 | Karami | ................. | A61F 13/025 602/43 |
| 5,308,313 | A | * | 5/1994 | Karami | ................. | A61F 13/025 602/54 |

(Continued)

FOREIGN PATENT DOCUMENTS

| WO | 93/19710 | 10/1993 |
| WO | 2005032401 | 4/2005 |
| WO | 2010061228 | 6/2010 |

OTHER PUBLICATIONS

The permeability of the dressing is measured by the method of the international standard EN 13726-2 dated Jun. 12, 2002.

*Primary Examiner* — Keri J Nelson
(74) *Attorney, Agent, or Firm* — Coloplast Corp., Coloplast A/S; Nick Baumann

(57) ABSTRACT

A method of preparing an adhesive wound dressing, the dressing comprising a central portion and an edge portion, the method comprising the steps of providing a support layer, drawing the support layer into a mold and dispensing a portion of uncured adhesive over the mold, distributing the adhesive in the mold and removing excess adhesive. The adhesive is cured and the support layer is detached from the mold. The central portion is provided with a plurality of through-going holes and an absorbent pad is placed on the non-adhesive side of the central portion and finally a backing layer is laminated to the absorbent pad and the edge portion of the support layer.

20 Claims, 2 Drawing Sheets

(52) U.S. Cl.
 CPC ...... *A61F 13/0226* (2013.01); *A61F 13/0253* (2013.01); *A61F 13/0289* (2013.01); *A61F 2013/00089* (2013.01)

(58) Field of Classification Search
 USPC .................................. 602/41–43, 47, 54, 55
 See application file for complete search history.

(56) References Cited

U.S. PATENT DOCUMENTS

| | | | | |
|---|---|---|---|---|
| 5,633,007 | A * | 5/1997 | Webb | A61F 13/023 424/443 |
| 8,080,703 | B2 * | 12/2011 | Marcussen | A61F 13/00995 128/887 |
| 2004/0126413 | A1 | 7/2004 | Gudmundur et al. | |
| 2010/0174250 | A1 * | 7/2010 | Hu | A61F 5/4401 604/319 |
| 2012/0095380 | A1 * | 4/2012 | Gergely | A61F 13/022 602/45 |

\* cited by examiner

WOUND DRESSING

This invention relates to a medical adhesive dressing. More specifically, the present invention is directed to a method of manufacturing a medical adhesive dressing comprising a backing film, a patterned adhesive layer and an absorbent pad.

BACKGROUND

An adhesive dressing is typically composed of an adhesive which is coated on a backing layer and the dressing is typically further provided with an absorbent layer e.g. in the form of an absorbent pad. Such an adhesive dressing should have adhesion suitable for firmly adhering the dressing to the skin and subsequently easily removing it from the skin. Furthermore, the dressing should have high water vapour permeability to avoid skin damage because it is directly attached to the skin, in which high water vapour permeability can promote wound healing.

Conventionally, the adhesive of dressings has the pressure-sensitive adhesive coated onto an entire surface of the backing layer. Thus, conventional dressings are disadvantageous in terms of low water vapour permeability, due to the coated adhesive per se, regardless of the water vapour permeability of the backing layer. That is, even though a backing layer having high water vapour permeability is used, the adhesive coated on the entire surface of the backing layer may prevent water vapour permeation, whereby the water vapour permeability of the dressing is reduced.

Wound dressings comprising soft adhesives, such as for example silicone, polyurethane or acrylate based adhesives are popular due to their softness. These soft adhesives are often solvent based and manufacturing dressings with these usually includes a drying or curing step and limited opportunity of modelling the adhesive after these steps.

Most of the known coating methods with such adhesives can only coat one uniform thickness at one time and the amount of waste in the process may be substantial.

If the absorbent pad is directly attached to the middle of the coated backing layer, the adhesive area between the absorbent pad and backing layer is largely wasted as it is not used for adhesion to the skin as intended. The adhesive, though formulated for good properties for skin contact, may not have the optimal properties for attaching the absorbent pad. For attachment of the absorbent pad, a cheaper or more effective adhesive or attachment method may be used.

An exposed absorbent pad on a backing layer requires good anchorage to the backing layer, especially when wet and heavy due to being soaked with exudate. By good anchorage is meant that absorption of moisture does not cause the absorbent pad and the backing layer to delaminate.

An exposed absorbent pad surface facing the wound side maximises the exudate absorption when in place. However, longer term placement (such as for a period longer than 3-5 days) on the wound may lead to ingrowth of tissue of the healing wound onto the absorbent core surface or more difficult removal, which in turn irritates the wound.

To overcome the removal problem, contact layers of less adhering nature are known. These contact layers are often thin films or gel layers having perforations to expose the absorbent core.

Another function of the contact layer may be to support and hold the absorbent core in position.

There is a need to simplify and improve the processes of dressing construction with different patterns and thicknesses of the different parts of the adhesive layer. There is a need to maximize the contact area to skin but minimize the coverage of the backing film.

SUMMARY OF THE INVENTION

An object of the present invention is to provide a method for producing an adhesive wound dressing with different patterns and thicknesses of the different parts of the adhesive layer.

Yet an object is to provide a method of producing an adhesive dressing, with reduced waste of adhesive.

An object is to provide a skin-friendly dressing with good moisture handling properties and good adherence to the skin.

An object is to provide an adhesive dressing with variable thickness of the adhesive layer.

DETAILED DESCRIPTION OF THE INVENTION

Figure 1:
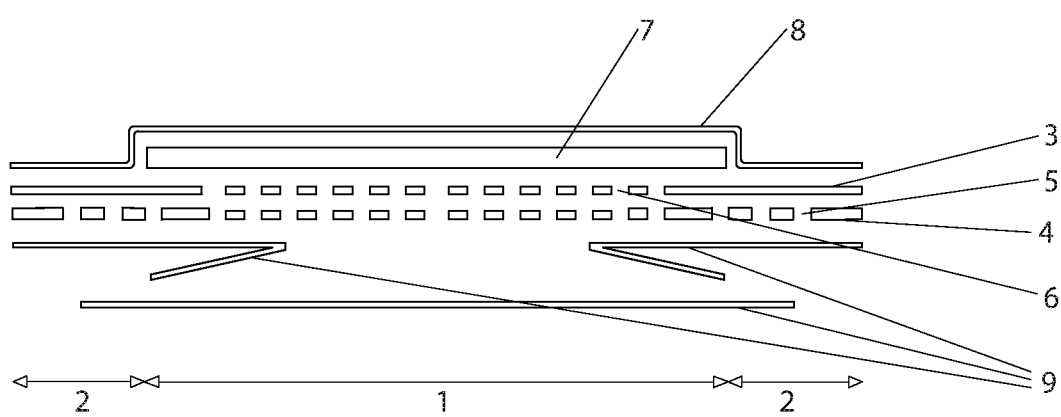
FIG. 1 illustrates an embodiment of the invention in cross-section (exploded view).

In a first aspect, the invention relates to a method of preparing an adhesive wound dressing, the dressing comprising a central portion and an edge portion, the method comprising the steps of: Providing a support layer, drawing the support layer into a mold, dispensing a portion of uncured adhesive over the mold, distributing the uncured adhesive in the mold, removing excess adhesive, curing the adhesive thereby providing an adhesive laminate consisting of the support layer and the cured adhesive, detaching the support layer from the mold, providing the central portion of the adhesive laminate with a plurality through-going holes, placing an absorbent pad on the non-adhesive side of the central portion of the support layer and laminating a backing layer to the absorbent pad and an edge portion of the support layer.

In a second aspect the invention relates to an adhesive wound dressing comprising a central portion and an edge portion, the dressing comprises a support layer being at least partly coated with an adhesive layer thus forming an adhesive laminate, the support layer of the edge portion of the dressing being continuous and the edge portion of the dressing being provided with a pattern of depressions in the adhesive layer and the central portion being provided with a plurality of through-going holes in the adhesive laminate, the dressing comprises an absorbent pad covering the central portion of the non skin facing surface of the support layer, and a backing layer being laminated to the absorbent pad and the edge portion of the support layer.

The edge portion of the dressing is surrounding the central portion to form an adhesive flange circumfending the central portion with the absorbent pad. Such construction is often called an island dressing. The dressing may be produced in many different sizes and shapes.

The width of a dressing may be from 2-40 cm, such as 5-35 cm, 7.5-30 cm, 10-20 cm or even 10-15 cm. The width of the dressing is measured at the broadest dimension of the dressing; a rectangular dressing having the dimensions of 10×20 cm has a width of 20 cm.

The edge portion may have a width of 1.5-6 cm, such as 2-5 cm, 2, 5-4.5 cm or even 2, 5-4 cm. The width of the edge portion is measured from the edge of the dressing to the outer edge of the absorbent pad of the central portion.

The absorbent pad may have a width of 2-30 cm, such as 3-25 cm, 3-20 cm, 3, 5-15 or even 4-13 cm.

The edge portion of the support layer being continuous should be understood as the layer is not provided with holes or apertures.

Molding the adhesive layer on a support layer makes it possible to optimize the permeability by reducing the thickness of the adhesive layer or even make sections without adhesive within the dressing. It is also possible to obtain different thicknesses of the adhesive layer within the same product. Different thicknesses provide different properties of the dressing, for example may a higher thickness at the edge portion provide a better adhesion or it may provide increased stiffness to the product. Other sections of the product may have reduced thickness in order to save material or to provide higher permeability and flexibility.

The thickness of the adhesive layer at the edge portion may be 150-500 µm, such as 200-450 µm, 250-450 µm or even 300-400 µm. The thickness of the adhesive layer at the central portion may be 75-250 µm, such as 100-200 µm, 125-175 µm or even 150 µm.

In one embodiment according to the first or second aspect of the invention a pattern of depressions may be molded in the edge portion of the adhesive layer. The depressions of the edge portion may penetrate a part of the adhesive layer or they may pass through the entire adhesive layer. The support layer at the depressions is not penetrated but remains intact. If the depressions penetrate the entire thickness of the adhesive layer, a neglectable amount of adhesive may however be present at the support layer at the bottom of the depressions. The depressions may enhance the permeability of the dressing as well as they may facilitate increased flexibility due to a thin layer of adhesive in the depressions. When the molded adhesive and the support layer are combined with a backing layer, it may be preferred to have depressions in the molded adhesive layer. By the here described molding process, it is possible to mold the adhesive layer so there are no or a reduced amount of adhesive at the sections where the depressions may be made.

At the edge portion of the dressing the double layer of films (backing layer and support layer) may provide a reservoir effect. The moisture passing through the adhesive coated support layer may be temporarily trapped in a void volume/the space between the support layer and the backing layer and subsequently evaporate through the backing layer. In this way the moisture will be removed fast from the skin surface and into this reservoir between the layers from where it may evaporate through the backing layer.

The support layer may be stretched during the molding process and the stretching may facilitate a higher permeability of the support layer and thereby easier passage of moisture away from the skin.

By stretching of the support layer the thickness of the layer may be altered for example from a starting thickness of 15-25 µm to a thickness of around 10 µm where it is thinnest. This may result in differentiated permeability of the layer. The support layer may be stretched up to 100%.

In one embodiment the void volumes between the support layer and the backing layer may comprise salt or other components that may enhance osmosis.

Wound dressings having different thickness of the adhesive layer, e.g. in the form of bevelled edges and indentations, are usually produced with a thermoplastic, non-curable adhesive such as a traditional hydrocolloid adhesive. Such dressings may be produced by coating a uniform thickness layer of adhesive on a film and then, by adding heat and pressure, forming the desired configuration of the dressing. Apart from being confined to use thermoplastic adhesives, this method of production also produces substantial amount of waste.

The through-going holes of the central portions may be made by punching, cutting or by applying high frequency mechanical vibrations, for example as disclosed in WO 2010/061228. As disclosed in WO 2010/061228, the size and shape of the through-going holes will correspond to the size and shape of the cross section of the perforating elements. By through-going is herein meant that the holes pass through both the support layer and the adhesive layer.

When making holes by applying high frequency mechanical vibrations, the support layer at the holes may melt to adhere to a temporary release liner (a release liner being present during the production process, but removed or substituted with a release liner for the final product). When the temporary release liner is removed, the residues of the support layer may be removed with it and the holes appear less frayed at the edge. The temporary release liner may be made from polyethylene (PE).

The central portion of the dressing may be provided with depressions during the molding process of the adhesive and the through going holes are then subsequently made in the depressions. This may save adhesive material in the process.

Through going holes may be arranged in a regular or random array, typically separated by 0.5 to 10 mm, such as 1-7 mm, such as 2-5 mm. The number of holes per dressing may be between 1 and 200, such as between 3 and 150, such as between 5 and 100, such as between 5 and 50 or even between 5 and 20. The number of through going holes per $cm^2$ of the central portion of the dressing may be 1-10, such as 1-7, such as 1-5 or even 2-5.

The holes in the central portion facilitate easy access for the wound exudates to enter into the absorbent pad. The holes may have a diameter of 0.5-10 mm, 1-8 mm, 1-5 mm, 1.5-5 mm, or even 2-4 mm.

The support layer may be any suitable layer being water impermeable but vapour permeable. A suitable support layer may be a polyurethane film.

The absorbent pad may be a uniform material or it may be a composite, for example in the form of a layered construction comprising layers of different texture and properties. The absorbent pad may comprise foam, cellulose, super absorbent particles or fibres or mixtures thereof. The absorbent pad may comprise a layer of foam facing the wound.

The absorbent pad may comprise a polyurethane foam.

The absorbent pad may comprise a super absorbing layer. The super absorbent layer may be combined with a layer of foam.

The absorbent pad may be bevelled in order to facilitate a smooth transition between the absorbent pad and the surrounding edge portion. Furthermore, the beveling may reduce the risk of pressure marks.

The adhesive may be a thermoset, curable adhesive. An example of such adhesive may be a silicone based adhesive. The adhesive may be a two-component system. Preferably, the adhesive contains no solvent. Preferred adhesives include polyurethane, acrylic, silicone or polyethylene or polypropylene oxide based cross-linking types as described in patent WO2005/032401. Or the adhesive may be a hotmelt type, which initially is heated to flow and subsequently cooled to gel or crosslink. Instead of curing upon cooling, the adhesive may in some embodiments cure upon application of thermal energy.

By molding the adhesive it may be possible to achieve beveled edges of the adhesive layer, even though the adhesive is a thermoset adhesive. Such adhesives may otherwise be difficult to produce in layers of variable thickness as they cannot be formed by exposing them to heat and pressure.

The thickness of the adhesive layer may be uniform or it may vary over the dressing, for example the adhesive layer in the central portion may be thinner than the thickness of the edge portion or vice versa. In this way, the adhesive layer may be tailor made for the dressing.

The support layer may be stretched before entering the mold. The stretching of the support layer in specific areas facilitates a higher permeability. The stretching of the support layer can also be used to change other properties of the layer. Stretching can be orientated so the layer will be more flexible in one direction than in another.

Stretching of the support layer and/or backing layer may also be used for obtain more space for expansion of the absorbent pad being integrated in the wound dressing. If either the support layer or the backing layer is stretched during the manufacturing of the dressing, it may be possible to provide more space for expansion of the absorbent pad.

The process, first preparing the support layer with adhesive coating and central holes, and then assembling the dressing with backing layer and absorbent pad in between render it possible to achieve a wound dressing with tailor made depressions, holes and thickness of the adhesive layer, and where the absorbent pad is entrapped between the support layer and the backing layer. The wound contacting surface will reduce risk of ingrowth of the wound but still facilitate rapid absorption of wound exudates due to the presence of the perforated adhesive layer.

The method of the invention combines the advantages of molding adhesive wafers e.g. for wound care with a solution where the central absorbent pad is enclosed between a backing film and an adhesive coated support layer. Hence it is possible to produce an absorbing wound care product with reduced waste and with a bacteria proof backing layer on one side and an adhesive coated support layer on the other.

The adhesive coated support layer of the dressing may be molded in an endless loop of molds. Afterwards holes may be made in the central portion in order to facilitate high permeability. An absorbent pad is placed on the non-adhesive side of the adhesive coated support layer. A high permeable backing layer is placed on top of the combination of support layer and absorption layer and the backing layer and the support layer are joined together, thereby enclosing the absorbent pad. The backing layer is preferably the same size as the support layer. A release liner protecting the adhesive surface before use may be added to the dressing.

The molding process provides the advantage of differentiated thickness of the adhesive layer in the same dressing and it will render it possible to design all kinds of dressing shapes without generating adhesive waste, as the adhesive is only added to the product in the cavity of the molds.

In one embodiment, the molding tool is cylindrical/drum-shaped, and the supporting surface is arranged to convey the liquid adhesive from an application area to a molding area in which the molding tool engages the adhesive. Moreover, the step of providing the adhesive and the step of forcing the molding tool into the adhesive may be performed concurrently.

The adhesive is in a liquid form during coating and becomes a form-stable mass upon coating. The adhesive may be a two-component system. Preferably, the adhesive contains no solvent.

In the context of the present invention the term "curing energy" shall be understood as any energy source suitable for curing the adhesive. Examples are thermal energy (heat), UV-radiation, IR-radiation or microwaves.

The absorbent pad and/or the adhesive layer may contain active ingredients, such as ibuprofen, paracetamol, silver compounds or other medically active ingredients adapted to reduce pain or to improve the healing of a wound. In one embodiment the absorbent pad comprises a silver compound with antimicrobial properties.

In one embodiment the dressing may comprise a silver compound in the form of a silver sodium hydrogen zirconium phosphate complex.

During the manufacturing process the adhesive material may reach a form-stable state without being fully reacted.

In the context of the present invention the term "form-stable" means that the material retains its shape under normal conditions, i.e. in the temperature range 25 to 130° C.

Full reaction or gelation may occur at a subsequent step of post-curing at which curing energy such as thermal energy may be provided to accelerate full reaction.

In order to achieve the predetermined pattern of the edge portion of the adhesive layer, the molding tool may comprise protrusions extending away from a base level of the molding tool i.e. towards the backing film during the molding process. It will be appreciated that the depressions will be defined by said protrusions, as the protrusions during application of pressure to the molding tool during molding will force the adhesive into the spaces defined between the protrusions of the molding tool.

The permeability of the central portion of the dressing may be at least 5000 gsm/24 h (gsm=grams per m$^2$).

The permeability of the edge portion of the dressing may be at least 1000 gsm/24 h (gsm=grams per m$^2$). The permeability of the dressing is measured by the method of the international standard EN 13726-2.

The absorbent pad may be adhered to the backing layer e.g. by welding in order to avoid delamination when wet.

The method opens up for producing a wide variety of shapes of the dressing with very little waste of material. Examples of dressing shapes may be rectangular, circular, elliptic or triangular.

DETAILED DESCRIPTION OF THE DRAWING

The invention will now be described in further detail with reference to the figures.

Figure 2:
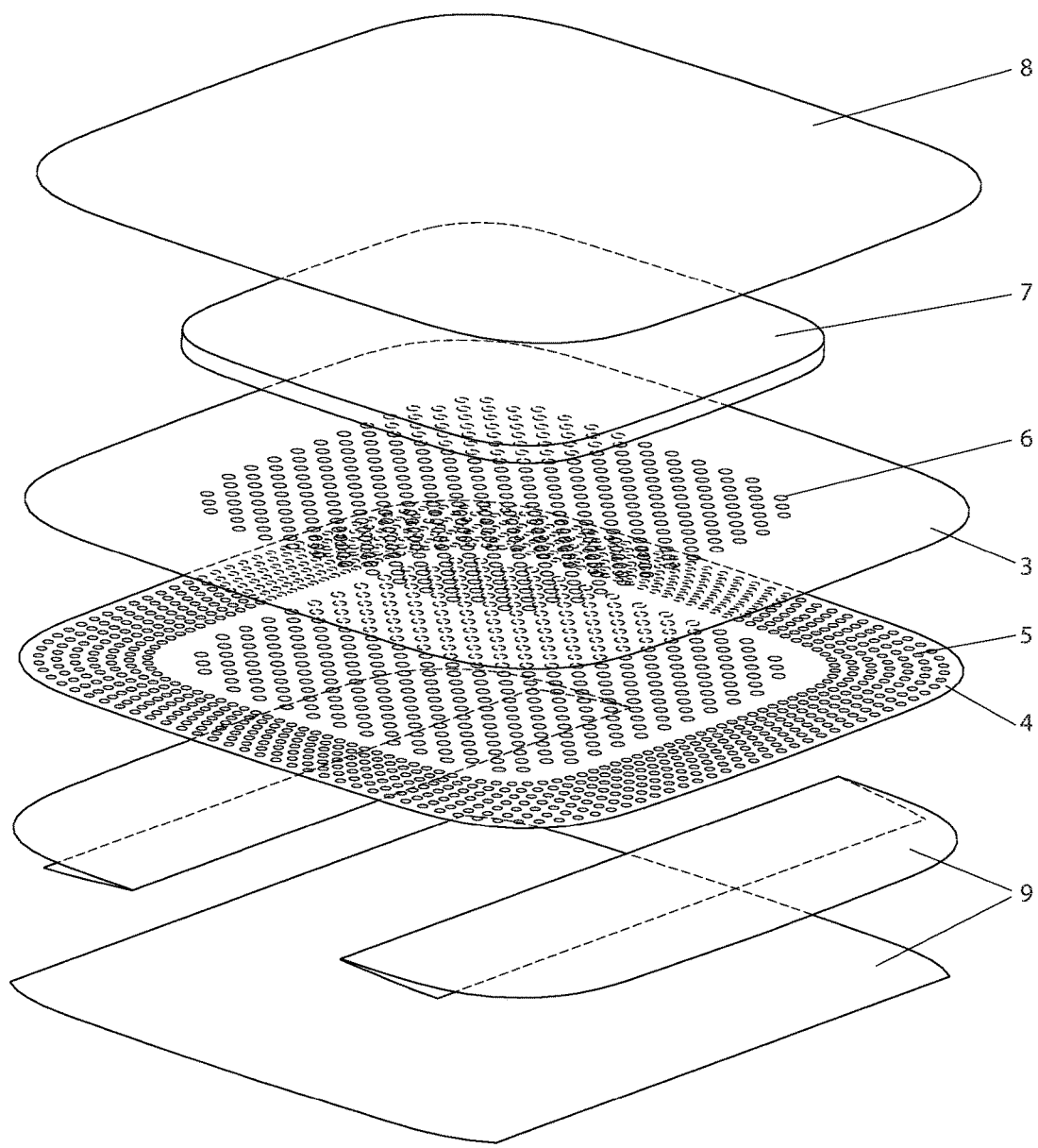
FIG. 2 discloses the embodiment in perspective (exploded view).

In FIGS. 1 and 2 are shown an embodiment of the invention in exploded cross-section and perspective view.

The dressing comprises a central portion (1) and an edge portion (2) surrounding the central portion (1). A support layer (3), e.g. in the form of a polyurethane film, is coated with a silicone adhesive layer (4) on the skin-facing surface. The edge portion of the adhesive layer (4) is provided with a pattern of depressions (5), the depressions (5) being in the adhesive layer (4) but not penetrating the support layer (3). The central portion of the adhesive coated support layer (3,4) is provided with a pattern of through going holes (6), the through-going holes (6) penetrating both the adhesive layer (4) and the support layer (3). On the non-adhesive side of the support layer is an absorbent pad (7), covering the central portion (1). The absorbent pad (7) may for example be a polyurethane foam sheet. The absorbent pad (7) may be bevelled at the edge portion. A backing layer (8) of substantially the same dimensions as the support layer (3) is laminated to the absorbent pad (7) and the edge portion (2) of the support layer (3). The backing layer (8) may be a polyurethane film of the same type as the support layer (3). The skin-facing adhesive surface of the dressing may be protected by one or more release liners (9) before use.

The invention claimed is:

1. An adhesive wound dressing comprising a central portion and an edge portion, the dressing comprising a support layer being at least partly coated with an adhesive layer to form an adhesive laminate, the support layer of the edge portion of the dressing being continuous and the edge portion of the dressing being provided with a pattern of depressions in the adhesive layer, the pattern of depressions being in the adhesive layer but not penetrating the support layer and the central portion being provided with a plurality of through-going holes in the adhesive laminate, the through-going holes penetrating both the support layer and the adhesive layer, the dressing comprising an absorbent pad covering the central portion of a non skin facing surface of the support layer and a backing layer laminated to the absorbent pad and the edge portion of the support layer, each of the plurality of through-going holes at least as large in the support layer as in the adhesive layer.

2. The dressing according to claim 1, wherein the adhesive layer is a thermoset, curable adhesive.

3. The dressing according to claim 1, wherein the absorbent pad comprises foam.

4. The dressing according to claim 1, wherein the absorbent pad comprises a super absorbing layer.

5. The dressing according to claim 1, wherein the holes in the central portion have a diameter of 1-10 mm.

6. The dressing according to claim 1, wherein a thickness of the adhesive layer in the central portion is thinner than the thickness of the adhesive layer in the edge portion.

7. The dressing according to claim 1, wherein a thickness of the adhesive layer in the central portion is 75-250 µm and a thickness of the adhesive layer in the edge portion is 150-500 µm.

8. The dressing according to claim 1, wherein each of the plurality of through-going holes is the same size in the support layer as in the adhesive layer.

9. The dressing according to claim 1, wherein each of the plurality of through-going holes is the same shape in the support layer as in the adhesive layer.

10. An adhesive wound dressing having a central portion and an edge portion surrounding the central portion, the dressing comprising:

a support layer extending across the central portion and the edge portion of the dressing;

a backing layer disposed on a non skin-facing surface of the support layer, the backing layer laminated to the support layer at the edge portion of the dressing;

an absorbent pad disposed between the support layer and the backing layer at the central portion of the dressing, the absorbent pad laminated to the backing layer; and an adhesive layer coating a skin-facing surface of the support layer, the adhesive layer defining a plurality of depressions in the adhesive layer at the edge portion of the dressing between a skin-facing surface of the adhesive layer and the support layer, the support layer and the adhesive layer defining a plurality of holes at the central portion of the dressing, each of the plurality of holes extending through the support layer and the adhesive layer from the skin-facing surface of the adhesive layer to the non-skin facing surface of the support layer, each of the plurality of holes at least as large through the support layer as through the adhesive layer, the support layer being unperforated along the edge portion of the dressing.

11. The dressing of claim 10, further including at least one release liner covering at least a portion of the skin-facing surface of the adhesive layer.

12. The dressing of claim 10, wherein the adhesive layer includes a thermoset adhesive.

13. The dressing of claim 10, wherein the absorbent pad includes a polyurethane foam sheet.

14. The dressing of claim 10, wherein the absorbent pad includes beveled edges.

15. The dressing of claim 10, wherein a thickness of the adhesive layer in the central portion of the dressing is less than the thickness of the adhesive layer in the edge portion of the dressing.

16. The dressing of claim 10, wherein at least one of the absorbent pad and the adhesive layer includes a medically active ingredient.

17. The dressing of claim 10, wherein each of the plurality of holes extending through the support layer and the adhesive layer have a diameter of 0.5 to 10 mm and a number of the plurality of holes is from 1 to 10 holes per $cm^2$.

18. The dressing of claim 10, wherein the backing layer and the support layer have substantially the same dimensions.

19. The dressing of claim 10, wherein each of the plurality of through-going holes is the same size in the support layer as in the adhesive layer.

20. The dressing of claim 10, wherein each of the plurality of through-going holes is the same shape in the support layer as in the adhesive layer.

* * * * *